United States Patent
Hong et al.

(10) Patent No.: US 8,247,797 B2
(45) Date of Patent: Aug. 21, 2012

(54) FIELD-EFFECT TRANSISTOR AND SENSOR BASED ON THE SAME

(75) Inventors: Seung Hun Hong, Seoul (KR); Byeong Ju Kim, Seoul (KR); Moon Sook Lee, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 218 days.

(21) Appl. No.: 12/814,824

(22) Filed: Jun. 14, 2010

(65) Prior Publication Data
US 2011/0147714 A1  Jun. 23, 2011

(30) Foreign Application Priority Data
Dec. 21, 2009  (KR) .................. 10-2009-0128381

(51) Int. Cl.
*H01L 29/775* (2006.01)
*H01L 29/78* (2006.01)
(52) U.S. Cl. ... 257/24; 257/253; 257/471; 257/E29.245; 257/E29.255

(58) Field of Classification Search .................... 257/24, 257/253, 471, E29.245, E29.255; 977/762, 977/742
See application file for complete search history.

(56) References Cited

U.S. PATENT DOCUMENTS

| | | | |
|---|---|---|---|
| 2006/0127904 A1 | 6/2006 | Segawa et al. | |
| 2007/0047172 A1 | 3/2007 | Wilbertz et al. | |
| 2010/0163843 A1* | 7/2010 | Choi et al. | 257/24 |
| 2011/0147708 A1* | 6/2011 | Radosavljevic et al. | 257/24 |
| 2011/0215339 A1* | 9/2011 | Murphy et al. | 257/76 |

FOREIGN PATENT DOCUMENTS

| | | |
|---|---|---|
| EP | 0311529 A2 | 4/1989 |
| JP | 2004132720 | 4/2004 |
| WO | 2005022142 A1 | 3/2005 |

OTHER PUBLICATIONS

Milgrew et al.; "A large transistor-based sensor array chip for direct extracellular imaging" Sensors and Actuators B, 2005, pp. 347-353.

* cited by examiner

*Primary Examiner* — David S Blum (57) ABSTRACT

A field-effect transistor has at least one electrode disposed independently of source and drain electrodes and in direct contact with the surface of a semiconductor channel to form a schottky barrier, so that it is possible to easily control the schottky barrier.

19 Claims, 5 Drawing Sheets

FIELD-EFFECT TRANSISTOR AND SENSOR BASED ON THE SAME

CROSS-REFERENCE TO RELATED APPLICATION

This application claims priority to Korean Patent Application No. 10-2009-0128381, filed on Dec. 21, 2009, and all the benefits accruing therefrom under 35 U.S.C. §119, the content of which in its entirety is herein incorporated by reference.

BACKGROUND

1) Field

The general inventive concept relates to a field-effect transistor and a sensor based on the field-effect transistor.

2) Description of the Related Art

A field-effect transistor ("FET") typically includes a source region that supplies electrons or holes, a drain region that depletes the electrons or the holes supplied from the source region, and a gate region that controls a flow of the electrons or the holes. The gate region may control the flow of the electrons or the holes using an electric field generated by the voltage applied to the gate.

The size of the conventional FET has been substantially reduced. Recently, chips including about 100 million transistors integrated thereon have been developed, wherein each of the 100 million transistors is about 50 nanometers (nm) in size. However, as the size of the transistor is reduced to below about 50 nm, the miniaturization of the FET may encounter a fundamental physical limitation. Accordingly, new elements such as silicon-on-insulator ("SOI") transistors, multi-gate transistors, and schottky transistors, for example, have been studied and developed to overcome fundamental physical limitation on further size reduction.

In addition, the FET may include a single-walled carbon nanotube having a semiconductor characteristic, e.g., a carbon nanotube transistor, having relatively high charge mobility. Researches on a high sensitivity sensor using the carbon nanotube have recently been made due to the characteristics of the carbon nonotube such as, e.g., a high charge mobility of the carbon nanotube transistor and the characteristic that all constituent atoms are located on a surface of the carbon nanotube and a chemical/biological reaction occurring on the surface of the carbon nanotube transistor is detected. A carbon nanotube-based sensor may measure the migration or charged state of charges in a chemical/biological reaction. Accordingly, the carbon nanotube-based sensor is based on a label-free method and has a short detection time. In addition, the cost of producing the carbon nanotube-based may be substantially reduced using a semiconductor process.

Recent developments in carbon nanotube growth and separation techniques may suggest that applications of the carbon nanotube, which are currently limited to bulk materials and composite materials, will be expanded to carbon nanotube-based electronic elements and sensors.

SUMMARY

Embodiments provide a field-effect transistor in which a schottky barrier is effectively adjusted and a sensor using the field-effect transistor.

According to an aspect, a field-effect transistor includes a substrate, a semiconductor channel disposed on the substrate, a source electrode and a drain electrode disposed on opposite ends of the semiconductor channel, respectively, and at least one additional electrode disposed independently of the source electrode and the drain electrode, where the at least one additional electrode is in direct contact with a surface of the semiconductor, and a schottky barrier is formed between the at least one additional electrode and the surface of the semiconductor channel.

In an embodiment, the source electrode, the drain electrode and the at least one additional electrode may be disposed substantially parallel to one another, and the semiconductor channel may be disposed substantially perpendicular to the source electrode, the drain electrode and the at least one additional electrode.

In an embodiment, the substrate may include one selected from the group consisting of a silicon wafer, a III-V group semiconductor substrate, a II-VI group semiconductor substrate, an epitaxially grown silicon-germanium (SiGe) substrate, a glass substrate, a quartz substrate, a metal substrate and a plastic substrate.

In an embodiment, the semiconductor channel may include at least one of a nanowire and a nanotube.

In an embodiment, the nanowire may include a material selected from the group consisting of silicon (Si), zinc oxide (ZnO), vanadium pentoxide ($V_2O_5$), gallium nitride (GaN), gallium phosphide (GaP), indium phosphide (InP), indium arsenide (InAs), gallium arsenide (GaAs), titanium oxide ($TiO_2$), tin oxide ($SnO_2$), aluminum nitride (AlN) and combinations thereof, and the nanotube may include at least selected from the group consisting of a single-walled nanotube, a multi-walled nanotube and a rope nanotube.

In an embodiment, a surface of at least one of the source electrode, the drain electrode and the semiconductor channel may be covered with an insulating material.

In an embodiment, each of the source electrode and the drain electrode may include a material selected from the group consisting of platinum (Pt), gold (Au), chrome (Cr), copper (Cu), aluminum (Al), nickel (Ni), palladium (Pd), titanium (Ti), molybdenum (Mo), lead (Pb), iridium (Ir), rhodium (Rh), cobalt (Co), tungsten (W), tantalum (Ta), erbium (Er), ytterbium (Yb), samarium (Sm), yttrium (Y), gadolinium (Gd), terbium (Tb), cerium (Ce) and a combination thereof.

In an embodiment, the at least one additional electrode may include a metal having a work function greater than a work function of a semiconductor when the semiconductor channel includes an n-type semiconductor material, and the at least one additional electrode may include a metal having a work function less than a work function of a semiconductor when the semiconductor channel includes a p-type semiconductor material.

In an embodiment, the at least one additional electrode includes a plurality of additional electrodes and an interval between the plurality of additional electrode is in a range from about 1 micrometer (μm) to about 20 micrometer (μm).

In an embodiment, a width of each of the plurality of additional electrodes is about twice a width of the semiconductor channel.

In an embodiment, the field-effect transistor may further include at least one of a gate electrode disposed under the substrate and a gate insulating layer disposed between the gate electrode and the substrate.

According to another aspect, a field-effect transistor-based sensor includes a semiconductor channel, a source electrode and a drain electrode disposed on opposite ends of the semiconductor channel, respectively, at least one additional electrode disposed independently of the source electrode and the drain electrode, where the at least one additional electrode is in direct contact with a surface of the semiconductor channel, and a schottky barrier is formed between the at least one additional electrode and the surface of the semiconductor channel and a reaction material attached to a surface of the at least one additional electrode, where the reaction material specifically has a specific affinity for a target material.

In an embodiment, at least one of a contact surface between the source electrode and the semiconductor channel and a contact surface between the drain electrode and the semiconductor channel may include a contact surface covered with an insulating material.

In an embodiment, the at least one additional electrode may include a metal having a work function greater than a work function of a semiconductor when the semiconductor channel includes an n-type semiconductor material, and the at least one additional electrode may include a metal having a work function less than a work function of a semiconductor when the semiconductor channel includes a p-type semiconductor material.

In an embodiment, the work function of the at least one additional electrode may change when the target material is specifically bound to the reaction material.

In an embodiment, at least one of a functional group and a linker molecule may be disposed on a surface of the at least one additional electrode, and the functional group and the linker molecule may react with the reaction material.

In an embodiment, the at least one additional electrode may include a plurality of additional electrodes, an interval between the plurality of additional electrode may be in a range from about 1 micrometer to about 20 micrometers, and a width of each of the plurality of additional electrodes may be about twice a width of the semiconductor channel.

In an embodiment, contact resistance due to a schottky barrier may be controlled by adjusting at least one of number, shape and size of the at least one additional electrode.

In an embodiment, the target material may include a material selected from the group consisting of a polynucleotide, a polypeptide, an oligosaccharide, a hormone, an organic molecule, a xenobiotic, a biomolecule, gas, a chemical material and a combination thereof.

BRIEF DESCRIPTION OF THE DRAWINGS

The above and other aspects of this disclosure will become more readily apparent by describing in further detail non-limiting example embodiments thereof with reference to the accompanying drawings, in which.

DETAILED DESCRIPTION

The general inventive concept now will be described more fully hereinafter with reference to the accompanying drawings, in which various non-limiting example embodiments are shown. This invention may, however, be embodied in many different forms, and should not be construed as limited to the example embodiments set forth herein. Rather, these example embodiments are provided so that this disclosure will be thorough and complete, and will fully convey the scope of the invention to those of ordinary skill in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the present claims.

<Field-Effect Transistor>

Figure 1:
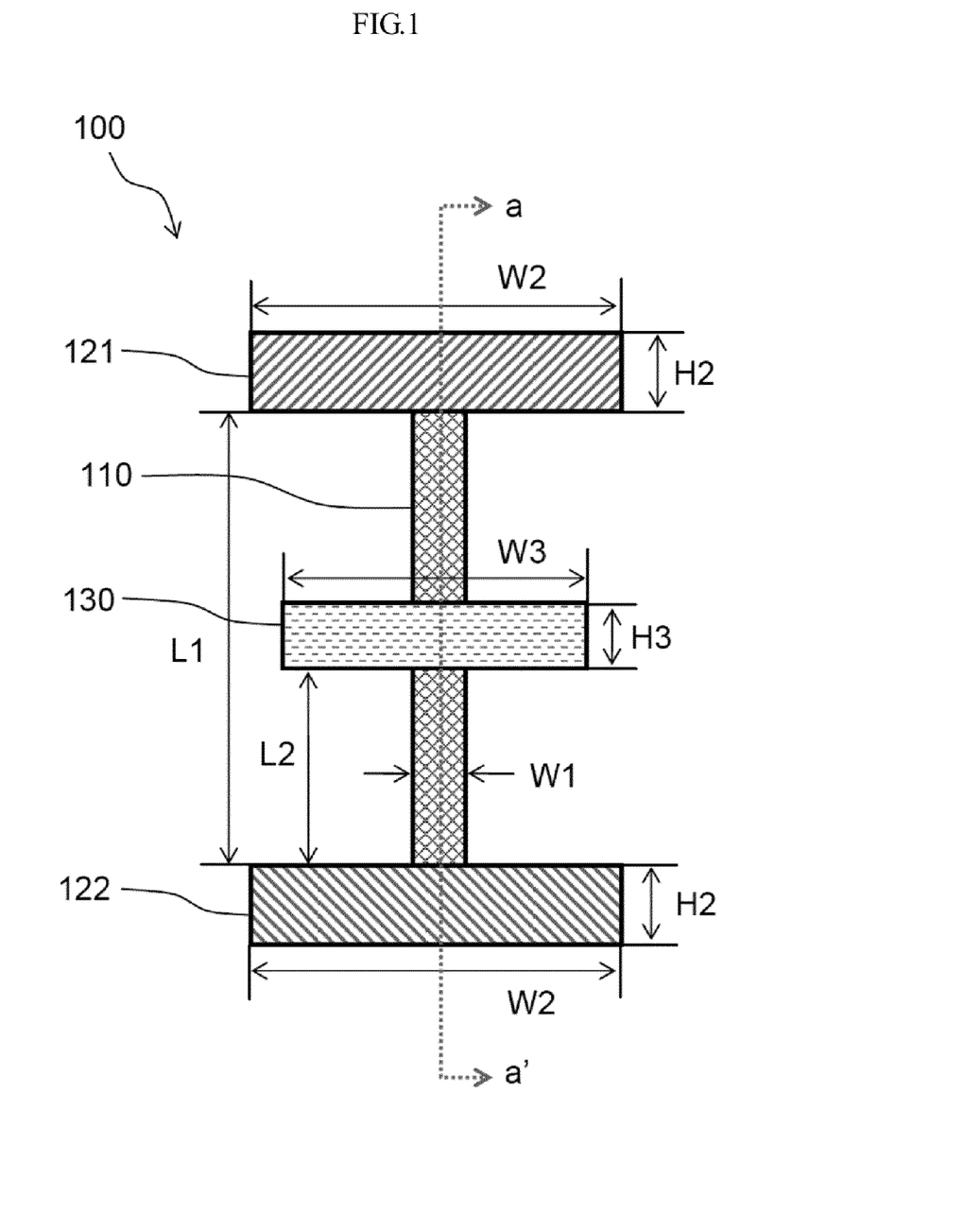
FIG. 1 is a top plan view of an embodiment of a field-effect transistor ("FET")
Figure 2:
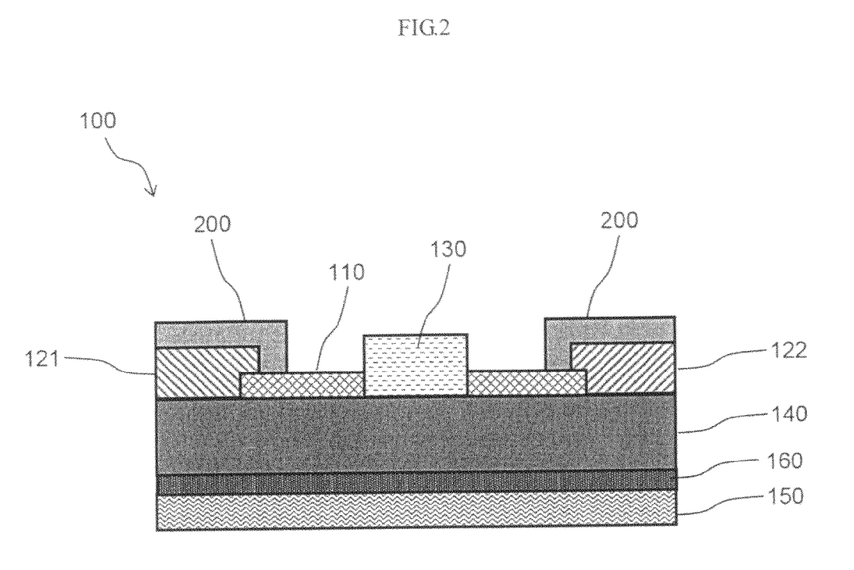
FIG. 2 is a cross-sectional view taken along line a-a' of FIG. 1.

FIG. 1 is a top plan view of an embodiment of a field-effect transistor ("FET"), and FIG. 2 is a cross-sectional view taken along line a-a' of FIG. 1.

Referring to FIGS. 1 and 2, the FET 100 includes a substrate 140, a semiconductor channel 110 disposed on the substrate 140, a source electrode 121 and a drain electrode 122 disposed on opposite end portions of the semiconductor channel 110, respectively, and at least one additional electrode 130 disposed independently of the source electrode 121 and the drain electrode 122, and a portion of a surface of the at least one additional electrode 130 and a portion of a surface of the semiconductor channel 110 are in direct contact and form a schottky barrier.

In an embodiment, the source electrode 121, the drain electrode 122 and the at least one additional electrode 130 may be disposed substantially parallel to one another and disposed apart from one another. The semiconductor channel 110 may be disposed substantially perpendicular to the source electrode 121, the drain electrode 122 and the at least one additional electrode 130.

In an embodiment, the FET operates as a schottky barrier transistor in which a schottky junction is formed by a contact between the at least one additional electrode 130 and the semiconductor channel 110. In an embodiment, a carrier transport speed of the FET may be substantially rapid and a threshold voltage of the FET may be substantially low. In an embodiment the threshold voltage of the FET may be in range of about 0.3 volts (V) to about 0.4 V, for example. Accordingly, the FET has a high efficiency and a high sensitivity at low voltage and high current.

In a conventional FET, the schottky barrier is formed by a contact between the source electrode 121 and the semiconductor channel 110 or between the drain electrode 122 and the semiconductor channel 110, and a contact resistance between the source electrode 121 and the semiconductor channel 110 or between the drain electrode 122 and the semiconductor channel 110 is thereby invariable or has a control limitation.

In an embodiment, the number of schottky barriers is changed by diversifying the size or number of the at least one additional electrode 130, and the contact resistance due to the schottky barrier is thereby effectively controlled.

The substrate 140 may be one of a silicon wafer, a III-V group semiconductor substrate, a II-VI group semiconductor substrate, an epitaxially grown SiGe substrate, a glass substrate, a quartz substrate, a metal substrate and a plastic substrate, for example, but not being limited thereto.

The semiconductor channel 110 disposed on the substrate 140 serves as a transducer. In an embodiment, the semiconductor channel 110 may be formed by forming a channel on the substrate 140, and adding a semiconductor material in the channel. The semiconductor material may be, for example, a nanowire or nanotube, but not being limited thereto.

The nanowire may include silicon (Si), zinc oxide (ZnO), vanadium pentoxide ($V_2O_5$), gallium nitride (GaN), gallium phosphide (GaP), indium phosphide (InP), indium arsenide (InAs), gallium arsenide (GaAs), titanium oxide ($TiO_2$), tin oxide ($SnO_2$) or aluminum nitride (AlN), for example, but not being limited thereto.

The nanotube may include a carbon nanotube. Carbon nanotubes are allotropes of carbon, in which one carbon atom is bonded with other carbon atoms in a hexagonal comb pattern that forms a tube, and are materials that have a substantially small diameter at a nanometer level. Carbon nanotubes typically have substantially improved mechanical properties, electrical selectivity and field emission characteristics. Carbon nanotubes exist in a state where at least one graphite sheet is rolled, and exhibit conductor or semiconductor characteristics depending on a rolled angle and shape. Carbon nanotubes may be categorized as single-walled nanotubes and multi-walled nanotubes according to the number of walls. Carbon nanotubes include rope nanotubes in which a plurality of single-walled nanotubes is bundled.

The size of the semiconductor channel 110 may vary. Referring again to FIG. 1, when a width W1 of the semiconductor channel 110 increases, a contact area between the semiconductor channel 110 and the at least one additional electrode 130 increases, and thus a schottky contact therebetween increases. When a length L1 of the semiconductor channel 110 increases, the number of at least one additional electrode 130 is increase, and thus the schottky contact increases. When the length L1 of the semiconductor channel 110 is longer than a certain length, a current characteristic deteriorates due to an increase in resistance. When the length L1 of the semiconductor channel 110 is less than a certain length, the number of the at least one additional electrodes 130 disposed is reduced, and thus the sensitivity of the sensor is lowered. In an embodiment, the length L1 of the semiconductor channel 110 may be predetermined according to the current characteristic and the sensitivity of the sensor. In an embodiment, the width W1 of the semiconductor channel 110 may be in a range from about 0.1 micrometers (μm) to about 10 μm, or from about 0.1 μm to about 5 μm, for example, and the length L1 of the semiconductor channel 110 may be in a range from about 0.1 μm to about 100 μm, or from about 10 μm to about 40 μm, for example.

The source electrode 121 or the drain electrode 122 may be formed of a semiconductor or metal. In an embodiment, the source electrode 121 or the drain electrode 122 may include platinum (Pt), gold (Au), chrome (Cr), copper (Cu), aluminum (Al), nickel (Ni), palladium (Pd), titanium (Ti), molybdenum (Mo), lead (Pb), iridium (Ir), rhodium (Rh), cobalt (Co), tungsten (W), tantalum (Ta), erbium (Er), ytterbium (Yb), samarium (Sm), yttrium (Y), gadolinium (Gd), terbium (Tb), cerium (Ce) or an alloy/alloys thereof, but not being limited thereto. When the source electrode 121 or the drain electrode 122 may be formed of a metallic material, the schottky barrier may be formed at a junction between the source electrode 121 and the semiconductor channel 110 or between the drain electrode 122 and the semiconductor channel 110.

As an area of the source electrode 121 or the drain electrode 122 increases, a current leakage may increase. In an embodiment, the area of the source electrode 121 or the drain electrode 122 may be predetermined to minimize a current leakage. In an embodiment, a surface of the source electrode 121 or a surface of the drain electrode 122 is covered with an insulating material, and oxidation or current leakage thereof is effectively prevented. In an embodiment, the insulating material may be an insulating polymer, but not being limited thereto.

The at least one additional electrode 130 is in contact with the semiconductor channel 110, and the schottky barrier is thereby formed at a junction therebetween. The term "schottky barrier" refers to a potential barrier formed at a metal-semiconductor junction. A contact characteristic of a contact between the metal and the semiconductor is theoretically dependent upon a work function of the metal and an electron affinity of the semiconductor in a state where no layer exists on an interface between the semiconductor and the metal and no mixture or diffusion occurs between the metal and the semiconductor. In other words, the potential barrier at the contact interface between the metal and the semiconductor is substantially equal to a difference between the work function and the electron affinity.

In an embodiment, the at least one additional electrode 130 may be made of a metallic material determined based on the material forming the semiconductor channel 110. When a schottky junction is formed between a metal and a n-type semiconductor, high-level electrons flow to the metal, and holes are located at sites corresponding to the electrons flowing from the semiconductor to the metal, and when a schottky junction is formed between a metal and a p-type semiconductor, electrons flow from the metal to the semiconductor, and holes flow from the semiconductor to the metal. Accordingly, the surface of the metal is in a positive polarity, whereas the surface of the semiconductor is in a negative polarity. Thus, the negative polarity of the surface of the semiconductor hinders migration of the electrons from the metal, thereby forming the schottky barrier.

In an embodiment, when the semiconductor channel 110 is formed of an n-type semiconductor material, at least one additional electrode 130 may be formed of a metal having a work function greater than a work function of the semiconductor channel 110, the schottky barrier is thereby formed therebetween. When the semiconductor channel 110 is formed of a p-type semiconductor material, the at least one additional electrode 130 may be formed of a metal having a work function less a work function that of the semiconductor channel 110, and the schottky barrier is thereby formed therebetween.

A size of the at least one additional electrode 130 is not especially limited. However, the width W3 of the at least one additional electrode 130 may be equal to or greater than the width W1 of the semiconductor channel 110 to form the schottky barrier by the contact with the semiconductor channel 110. When the width W3 of the at least one additional electrode 130 is less than a certain width, a damage effect may occur at both ends of the at least one additional electrode 130. Accordingly, in an embodiment, the width W3 of the at least one additional electrode 130 is at least twice the width W1 of the semiconductor channel 110, but not being limited thereto.

Figure 3:
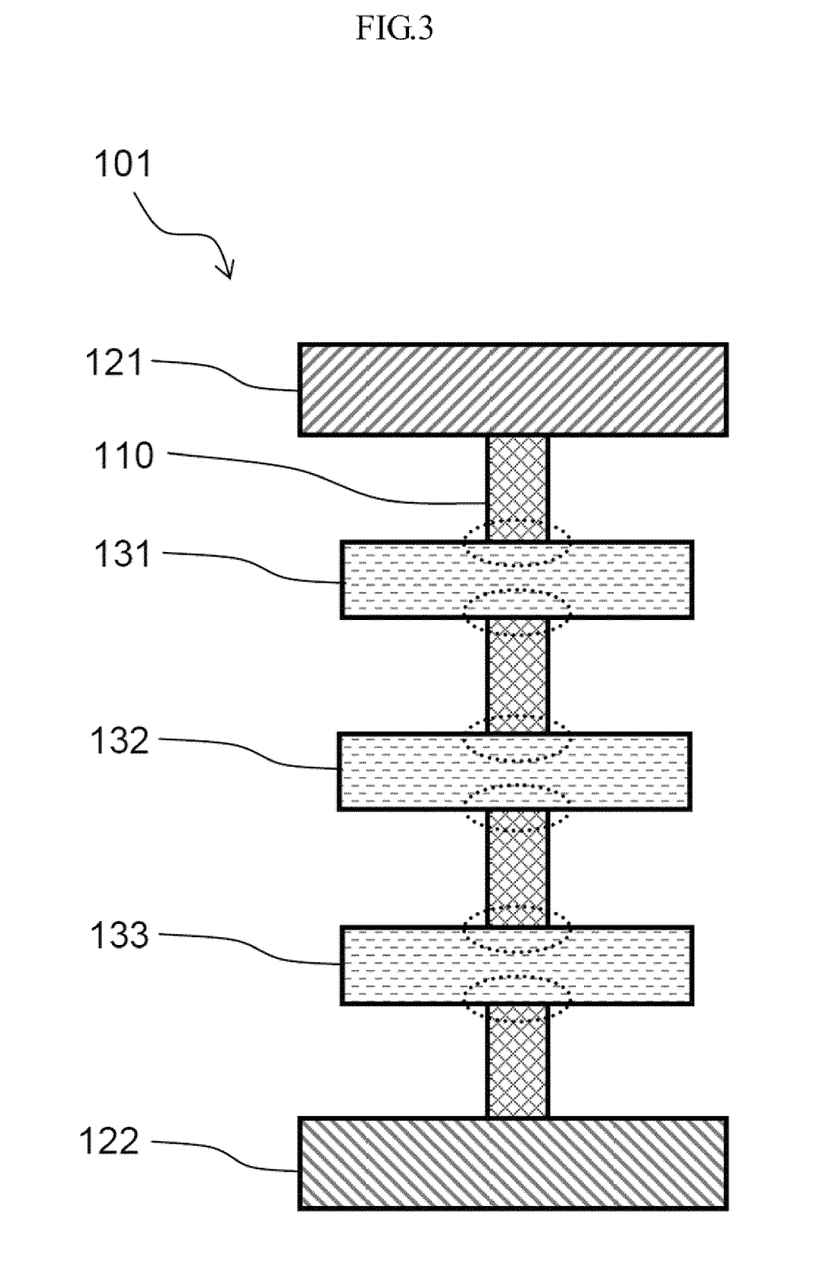
FIG. 3 is a top plan view of an another embodiment of an FET.

The number of the at least one additional electrodes 130 may be more than one. As the number of the at least one additional electrodes 130 increases, the number of schottky barriers increases. As shown in FIG. 3, the FET may include more than one additional electrode, e.g., a first additional electrode 131, a second additional electrode 132 and a third additional electrode 133, each of the more than one additional electrode has two contacts with the semiconductor channel 110. When a number of the more than one additional electrode in the FET is "n", the number of schottky barriers is "2n" (shown as dotted circles of FIG. 3). When the number of the at least one additional electrodes 130 is greater than a certain number, contact resistance substantially increases. Accordingly, the number of the at least one additional electrodes 130 may be determined base on the length of the semiconductor channel 110. In an embodiment, the number of the at least one additional electrode 130 may be, for example, from 2 to 10 or from 3 to 8. In an embodiment, the interval between two adjacent electrodes of the more than one additional electrode, e.g., the first additional electrode 131, the second additional electrode 132 and the third additional electrode 133 may vary, and the interval between the source electrode 121 and the additional electrode disposed adjacent to the source electrode among the more than one additional electrode, e.g., the first additional electrode 131, or the interval between the drain electrode 122 and the additional electrode disposed adjacent to the drain electrode among the more than one additional electrode, e.g., the third additional electrode 133, may vary. The intervals described above may be determined within a range in which no interference occurs in consideration of the length L1 of the semiconductor channel 110 and a height H3 of the additional electrode 130. In an embodiment, the interval between two adjacent electrodes of the more than one additional electrode, the interval between the source electrode 121 and the additional electrode disposed adjacent to the source electrode among the more than one additional electrode and the additional electrode disposed adjacent to the drain electrode among the more than one additional electrode, for example, may be in a range from about 1 micrometer (μm) to about 20 μm, from about 1 μm to about 10 μm or from about 2 μm to about 5 μm.

A shape of the at least one additional electrode 130 may vary. In an embodiment, the at least one additional electrode 130 may be in a bar shape, a circular shape, an elliptical shape, a quadrilateral shape or a rhombic shape, for example, but not being limited thereto.

In an embodiment, the FET may include a gate electrode 150. As shown in FIG. 2, the gate electrode 150 may be disposed below the substrate 140, and a gate insulating layer 160 may be disposed between the gate electrode 150 and the substrate 140.

<FET-Based Sensor>

Figure 4:
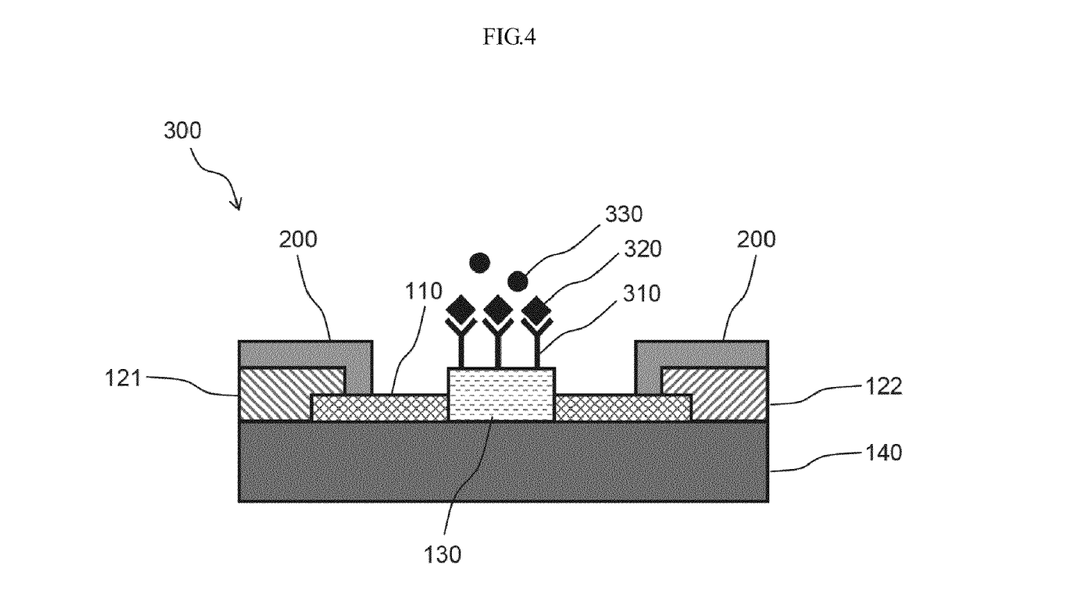
FIG. 4 is a cross-sectional view of an embodiment of an FET-based sensor.

FIG. 4 is a cross-sectional view of an embodiment of an FET-based sensor. The same or like elements shown in FIG. 4 have been labeled with the same reference characters as used above to describe embodiments of FET as shown in FIGS. 1 through 3, and any repetitive detailed description thereof will hereinafter be omitted or simplified.

Referring to FIG. 4, a FET-based sensor 300 includes a semiconductor channel 110, a source electrode 121 and a drain electrode 122 disposed on opposite ends of the semiconductor channel 110, respectively, at least one additional electrode 130 disposed independently of the source electrode 121 and the drain electrode 122, where a portion of a surface of the at least one additional electrode 130 and a portion of a surface of the semiconductor channel 110 are in direct contact and form a schottky barrier, and a reaction material 310 attached to a surface of the at least one additional electrode 130 and that has a specific affinity for a target material 320 to be detected.

The FET-based sensor 300 detects the target material 320 by detecting change in electrical conductivity resulting from change of the schottky barrier. In an embodiment, when a sample including the target material 320 is provided to the reaction material 310 corresponding to the reaction material 310 attached on the surface of the at least one additional electrode 130, the FET-based sensor 300 may detect the target material 320 by measuring a value of current flowing through the semiconductor channel 110 and comparing the measured current value with a current value when no reaction occurs.

Hereinafter, the detection principle will be described in greater detail. When the reaction material 310 is specifically bound to the target material 320, a work function of the at least one additional electrode 130 changes, and contact resistance caused by a schottky barrier formed at a junction between the at least one additional electrode 130 and the semiconductor channel 110 thereby changes. In other words, the change of the work function of the at least one additional electrode 130 is reflected in the electrical conductivity of the semiconductor channel 110. Thus, by detecting the change of the work function of the at least one additional electrode 130, the FET-based sensor 300 may sense whether the reaction material 310 is specifically bound to the target material 320. In an embodiment, when the at least one additional electrode 310 made of Au, for example, and the semiconductor channel 110 made of a carbon nanotube, for example, form a schottky junction, and when the reaction material 310, e.g., single-stranded deoxyribonucleic acid ("DNA"), attached to the surface of the at least one additional electrode 130 reacts with target DNA having a sequence complementary to a sequence of the single-stranded DNA, the work function of the at least one additional electrode 130 is lowered. Thus, the schottky barrier becomes higher so that the contact resistance increases, and the electrical conductivity of the semiconductor channel 110 is thereby lowered. Therefore, by measuring the change of electrical conductivity, the target material 320 is effectively detected.

In contrast, when the target material 320 is detected using the schottky barrier formed at the junctions between the source electrode 121 and the semiconductor channel 110, and between the drain electrode 122 and the semiconductor channel 110, the schottky barrier may not be effectively controlled, and thus there is a limitation to improving detection sensitivity. In addition, when the reaction material 310 is attached to surfaces of the source electrode 121 and the drain electrode 122, current leakage occurs at the source electrode 121 and the drain electrode 122, which are connected to a power source and have a wide surface area and thus detection sensitivity is lowered.

In an embodiment, the at least one additional electrode 130 of the FET based sensor 300 is attached to the surface of the semiconductor channel 110, thereby forming the schottky barrier. Since the number of the schottky barriers may be increased by adjusting the number of the at least one additional electrodes 130, a change in current increases when the target material 320 reacts with the reaction material 310, so that detection sensitivity is improved. Further, the reaction material 310 is attached to the surface of the at least one additional electrode 130, and the surfaces of the source and drain electrodes 121 and 122 are covered with an insulating material, thereby making it possible to form an insulating layer 200 and minimize the current leakage.

A material forming the at least one additional electrode 130 may be selected in consideration of a material of which the semiconductor channel 110 is formed. As mentioned in section 1 above, when the semiconductor channel 110 is made of an n-type semiconductor material, the at least one additional electrode 130 may be formed of a metal having a work function greater than the work function of the semiconductor. In an embodiment, when the semiconductor channel 110 is made of a p-type semiconductor material, the at least one additional electrode 130 may be formed of a metal having a work function less than the work function of the semiconductor. In an embodiment, the number of the at least one additional electrodes 130 may be plural, and an interval between the at least one additional electrode 130 or an interval between the source electrode 121 and the at least one additional electrode 130 disposed adjacent to the source electrode 121 or between the drain electrode 121 and the at least one additional electrode 130 disposed adjacent to the drain electrode 121 may be in a range from about 1 μm to about 20 μm. A width of the at least one additional electrode 130 may be at least twice as wide as the semiconductor channel 110.

The reaction material 310 is a material that has a specific affinity for the target material 320. Here, the term "target material" refers to a target to be detected, and may be, for example, a biomolecule, a gas molecule or a chemical material. Specific binding of the reaction material 310 to the target material 320 means that the reaction material 310 is not bound to a material 330 other than the target material 320. In an embodiment, the target material having a specific base sequence may give rise to a hybridization reaction with the reaction material having a complementary base sequence. Here, the term "hybridization" means that a single-stranded polynucleotide probe reacts with its complementary polynucleotide to thereby form polynucleotide of a double helix structure.

The reaction material 310 is physically or chemically adsorbed and attached to the surface of the at least one additional electrode 130. To facilitate this adsorption and attachment, the surface of the at least one additional electrode 130 may be modified. In an embodiment, the surface of the at least one additional electrode 130 may be modified to contain, for example, either a reactive functional group such as an amino group, a carboxyl group, an oxo group and a thiol group, or a linker molecule. In an embodiment, the reaction material 310 may have one end to which a functional group bound to the reactive functional group of the surface of the at least one additional electrode 130 can be bonded. In an embodiment, the surface of the at least one additional electrode 130 may be modified using aldehyde group (—CHO), and the end of the reaction material 310 may be attached with amine group ($NH_2$).

The number of the schottky barriers increases by adjusting the number of the at least one additional electrodes 130 and a size of the contact between the at least one additional electrode 130 and the semiconductor channel 110. In an embodiment, the number of the schottky barriers is effectively controlled through the adjustment of the number, size and/or shape, of the at least one additional electrode 130, for example.

The target material 320 may include, for example, a biomolecule. The reaction material 310 may include a probe that has a specific affinity for the biomolecule. The biomolecule or the probe may include polynucleotide such as deoxyribonucleic acid ("DNA"), ribonucleic acid ("RNA"), peptide nucleic acid ("PNA"), locked nucleic acid ("LNA") or a hybrid thereof; polypeptide such as an antibody or antigen subunit (e.g., a binding partner such as a monoclonal antibody, a polyclonal antibody or a complementarity determining region ("CDR")), an enzyme, a substrate, a ligand, an aptamer or a receptor; oligosaccharide; a hormone; an organic molecule; or a xenobiotic. The specific binding of the target material 320 to the reaction material 310 may include a polynucleotide-polynucleotide binding, an antibody-polynucleotide binding, an antibody-hormone binding, an antibody-xenobiotic binding or an antibody-polypeptide binding.

The term "polynucleotide" generally designates any poly-RNA or -DNA such as an unmodified or modified RNA or DNA. "Polynucleotide" includes, but not limited to, a hybrid molecule including single- or double-stranded DNA, DNA that is a mixture of single- or double-stranded regions, single- or double-stranded RNA, RNA that is a mixture of single- or double-stranded regions, single- or double-stranded DNA and RNA, or DNA and RNA that are a mixture of single- or double-stranded regions. Further, "polynucleotide" includes triple-stranded regions including RNA, DNA or both RNA and DNA. Also, "polynucleotide" includes relatively short polynucleotides called oligonucleotides. In addition, "polynucleotide" includes PNAs called artificial DNA analogues, plasmid DNAs or engineered DNAs.

The term "polypeptide" refers to any peptide or protein having two or more amino acids joined through peptide bonds or modified peptide bonds. "Polypeptide" includes short chains such as peptides, oligopeptides or oligomers, and long chains such as proteins. "Polypeptide" includes amino acid sequences modified by natural processes or chemical modification techniques known in the art. Such modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediation addition of amino acids to proteins, such as arginylation and ubiquitination.

In an embodiment wherein the target material 320 is a gas molecule, the FET-based sensor 300 may function as a gas sensor. In an embodiment, the reaction material 310, e.g., palladium (Pd) nanoparticles, that selectively recognizes hydrogen gas, is coated on the surface of the at least one additional electrode 130, so that a hydrogen sensor is formed. In another embodiment, the reaction material 310, e.g., starch, that selectively recognizes carbon dioxide, is coated on the surface of the at least one additional electrode 130, so that a carbon dioxide sensor is formed. Polymers and conductive fluoropolymers as the reaction material 310 are immobilized on the surface of the at least one additional electrode 130, so that the sensor can detect dimethyl methylphosphonate ("DMMP") that is a stimulant of nerve gas sarin.

An experiment according to the present inventive concept will now be described in detail.
<Experiment>

An embodiment of FET shown in FIG. 1 was manufactured as an element of the experiment. The width W1 and length L1 of the semiconductor channel 110 were set to about 2 µm and about 30 µm, respectively. The width W2 and height H2 of the source electrode 121 and the drain electrode 122 were set to about 10 µm and about 4 µm, respectively. The width W3 and height H3 of the at least one additional electrode 130 were set to about 12 µm and about 4 µm, respectively. The interval between the electrodes was set to about 4 µm.

The FET manufactured was mounted in an electrochemical cell, and then a bias voltage of about 0.1 V was continuously applied between the source electrode 121 and the drain electrode 122. In the experiment, the cell was filled with a phosphate buffer solution ("PBS") of 9 ml.

Figure 5:
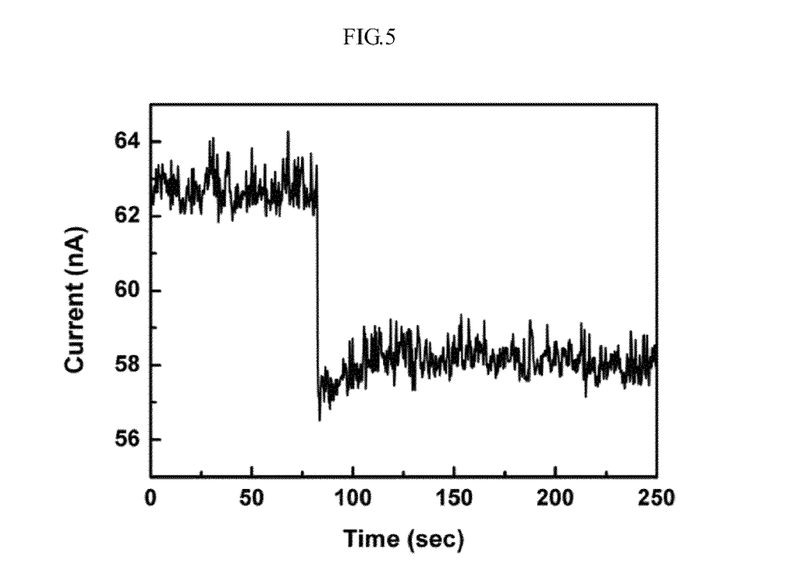
FIG. 5 is a graph of current (nanoampere) versus time (second) showing a current variation in Example 1 of an experiment according to the present inventive concept.
Figure 6:
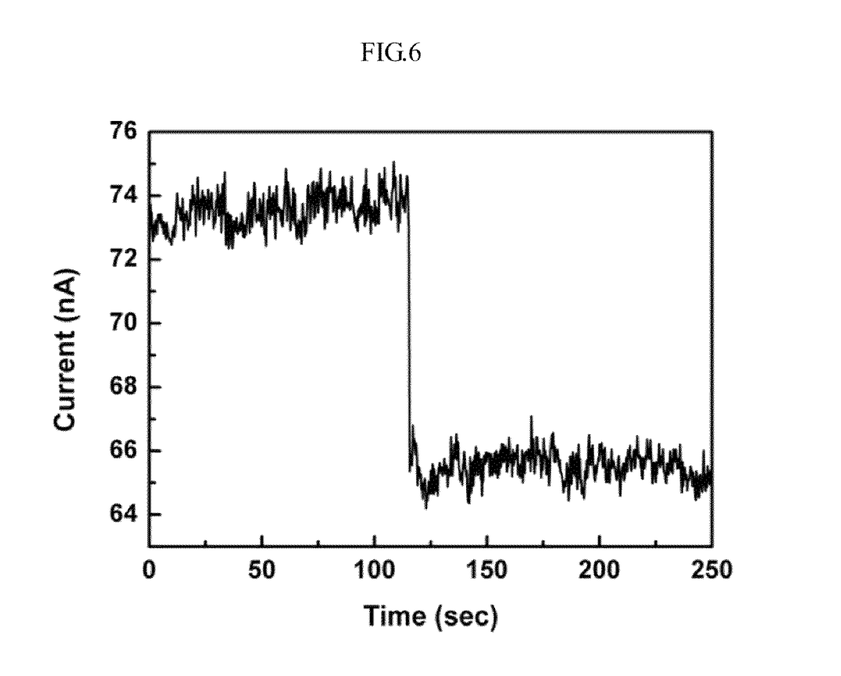
FIG. 6 is a graph of current (nanoampere) versus time (second) showing a current variation in Example 2 of the experiment.
Figure 7:
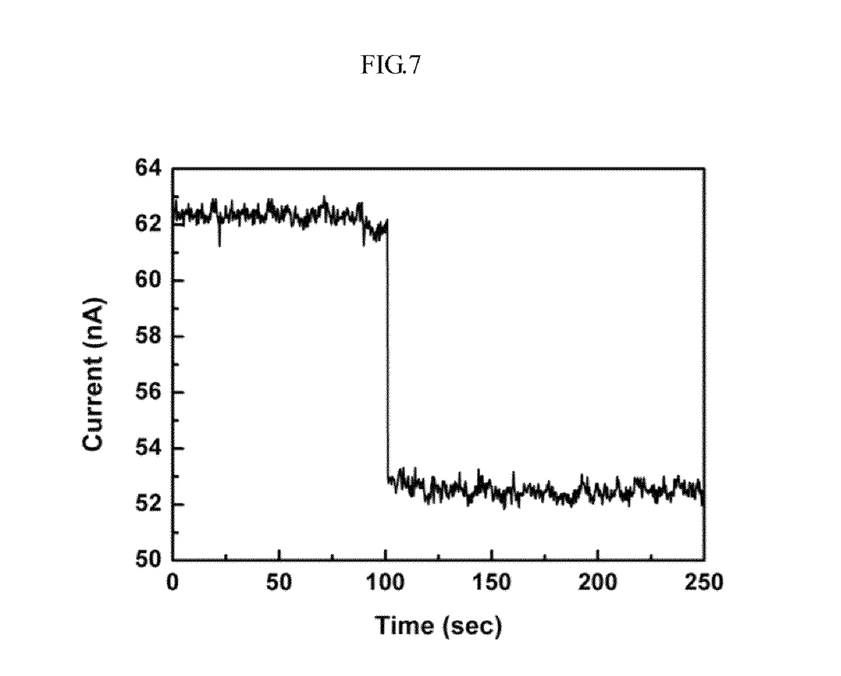
FIG. 7 is a graph of current (nanoampere) versus time (second) showing a current variation in Example 3 of the experiment.

When an element of the experiment was stabilized while showing constant current, a DNA solution of 100 nanomolar (nM) was injected into the cell using a micro-pipette, and a current change was observed. With respect to other elements of the experiment having a semiconductor channel 110 of a same size, a DNA detection test was carried out while varying the number of the at least one additional electrode 130 as in Table 1 below, and the results are shown in Table 1 and FIGS. 5 through 7.

TABLE 1

| Example | Number of Additional Electrodes | Variation in Quantity of Charge |
| --- | --- | --- |
| 1 | 1 | About 7% |
| 2 | 3 | About 12% |
| 3 | 5 | About 16% |

Example 1 having one additional electrode showed a variation of about 7% to about 8%, Example 2 having three additional electrodes showed a variation of about 12%, and Example 3 having five additional electrodes showed a variation of about 16%.

In the experiment, as the number of the at least one additional electrode increases, a variation in the quantity of charge, i.e. a variation in current, becomes greater when the DNA is detected.

The general inventive concept should not be construed as being limited to the embodiments set forth herein. Rather, these embodiments are provided so that this disclosure will be thorough and complete and will fully convey the concept of the present invention to those of ordinary skill in the art.

While the general inventive concept has been particularly shown and described with reference to embodiments thereof, it will be understood by those of ordinary skill in the art that various changes in form and details may be made therein without departing from the spirit or scope of the present invention as defined by the following claims.

What is claimed is:

1. A field-effect transistor comprising:
   a substrate;
   a semiconductor channel disposed on the substrate;
   a source electrode and a drain electrode disposed on opposite ends of the semiconductor channel, respectively; and
   at least one additional electrode disposed independently of the source electrode and the drain electrode,
   wherein the at least one additional electrode is in direct contact with a surface of the semiconductor channel forming a schottky barrier between the at least one additional electrode and the surface of the semiconductor channel.

2. The field-effect transistor according to claim 1, wherein the source electrode, the drain electrode and the at least one additional electrode are disposed substantially parallel to one another, and
   the semiconductor channel is disposed substantially perpendicular to the source electrode, the drain electrode and the at least one additional electrode.

3. The field-effect transistor according to claim 1, wherein the substrate includes one selected from the group consisting of a silicon wafer, a III-V group semiconductor substrate, a II-VI group semiconductor substrate, an epitaxially grown silicon-germanium substrate, a glass substrate, a quartz substrate, a metal substrate and a plastic substrate.

4. The field-effect transistor according to claim 1, wherein the semiconductor channel comprises at least one of a nanowire and a nanotube.

5. The field-effect transistor according to claim 4, wherein the nanowire includes a material selected from the group consisting of silicon, zinc oxide, vanadium pentoxide, gallium nitride, gallium phosphide, indium phosphide, indium arsenide, gallium arsenide, titanium oxide, tin oxide, aluminum nitride and combinations thereof, and the nanotube includes at least one selected from the group consisting of a single-walled nanotube, a multi-walled nanotube and a rope nanotube.

6. The field-effect transistor according to claim 1, wherein a surface of at least one of the source electrode, the drain electrode and the semiconductor channel is covered with an insulating material.

7. The field-effect transistor according to claim 6, wherein each of the source electrode and the drain electrode includes a material selected from the group consisting of platinum, gold, chrome, copper, aluminum, nickel, palladium, titanium, molybdenum, lead, iridium, rhodium, cobalt, tungsten, tantalum, erbium, ytterbium, samarium, yttrium, gadolinium, terbium, cerium and a combination thereof.

8. The field-effect transistor according to claim 1, wherein
the at least one additional electrode includes a metal having a work function greater than a work function of a semiconductor when the semiconductor channel includes an n-type semiconductor material, and
the at least one additional electrode includes a metal having a work function less than a work function of a semiconductor when the semiconductor channel includes a p-type semiconductor material.

9. The field-effect transistor according to claim 8, wherein an interval between the at least one additional electrode is in a range from about 1 micrometer to about 20 micrometers.

10. The field-effect transistor according to claim 8, wherein a width of the at least one additional electrode is about twice a width of the semiconductor channel.

11. The field-effect transistor according to claim 1, further comprising
at least one of a gate electrode disposed under the substrate and a gate insulating layer disposed between the gate electrode and the substrate.

12. A field-effect transistor-based sensor comprising:
a semiconductor channel;
a source electrode and a drain electrode disposed on opposite ends of the semiconductor channel, respectively;
at least one additional electrode disposed independently of the source electrode and the drain electrode, wherein the at least one additional electrode is in direct contact with a surface of the semiconductor channel forming a schottky barrier between the at least one additional electrode and the surface of the semiconductor channel; and
a reaction material attached to a surface of the at least one additional electrode, wherein the reaction material has a specific affinity for a target material.

13. The field-effect transistor-based sensor according to claim 12, wherein at least one of a contact surface between the source electrode and the semiconductor channel and a contact surface between the drain electrode and the semiconductor channel includes a contact surface covered with an insulating material.

14. The field-effect transistor-based sensor according to claim 12, wherein
the at least one additional electrode includes a metal having a work function greater than a work function of a semiconductor when the semiconductor channel includes an n-type semiconductor material, and
the at least one additional electrode includes a metal having a work function less than a work function of a semiconductor when the semiconductor channel includes a p-type semiconductor material.

15. The field-effect transistor-based sensor according to claim 14, wherein the work function of the at least one additional electrode changes when the target material is specifically bound to the reaction material.

16. The field-effect transistor-based sensor according to claim 15, wherein
at least one of a functional group and a linker molecule is disposed on a surface of the at least one additional electrode, and
the functional group and the linker molecule react with the reaction material.

17. The field-effect transistor-based sensor according to claim 14, wherein
the at least one additional electrode includes a plurality of additional electrodes,
an interval between the plurality of additional electrode is in a range from about 1 micrometer to about 20 micrometers, and
a width of each of the plurality of additional electrodes is about twice a width of the semiconductor channel.

18. The field-effect transistor-based sensor according to claim 12, wherein contact resistance due to a schottky barrier is controlled by adjusting at least one of number, shape and size of the at least one additional electrode.

19. The field-effect transistor-based sensor according to claim 12, wherein the target material includes a material selected from the group consisting of a polynucleotide, a polypeptide, an oligosaccharide, a hormone, an organic molecule, a xenobiotic, a biomolecule, a chemical material and a combination thereof.

* * * * *